(12) United States Patent
Kadobayashi et al.

(10) Patent No.: US 8,986,008 B2
(45) Date of Patent: Mar. 24, 2015

(54) METHOD OF ARRANGING ARTIFICIAL MOLAR TEETH

(71) Applicant: Kabushiki Kaisha Shofu, Kyoto-shi, Kyoto (JP)

(72) Inventors: Yusei Kadobayashi, Kyoto (JP); Toshihide Fujii, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 107 days.

(21) Appl. No.: 13/961,308

(22) Filed: Aug. 7, 2013

(65) Prior Publication Data

US 2013/0316304 A1    Nov. 28, 2013

Related U.S. Application Data

(63) Continuation of application No. 12/638,405, filed on Dec. 15, 2009, now abandoned.

(30) Foreign Application Priority Data

Dec. 17, 2008  (JP) ................................. 2008-320433
Oct. 22, 2009  (JP) ................................. 2009-243379

(51) Int. Cl.
A61C 13/10    (2006.01)
A61C 13/08    (2006.01)
A61C 13/097   (2006.01)

(52) U.S. Cl.
CPC .............. *A61C 13/08* (2013.01); *A61C 13/097* (2013.01); *A61C 13/10* (2013.01)
USPC ........................................................ 433/196

(58) Field of Classification Search
CPC .... A61C 13/00; A61C 13/0024; A61C 13/08; A61C 13/097; A61C 13/10; A61C 13/1016; A61C 13/102; A61C 13/12

USPC ......... 433/72, 167, 171, 196, 203.1, 215, 229
See application file for complete search history.

(56) References Cited

U.S. PATENT DOCUMENTS 1,657,673 A    1/1928  Gysi
1,822,837 A    9/1931  Avery et al.
(Continued)

FOREIGN PATENT DOCUMENTS

GB    4906186      3/1990
JP    11-290347   10/1999
(Continued)

OTHER PUBLICATIONS

Japanese Notification of Reason for Refusal mailed Mar. 5, 2013 in corresponding Japanese Application No. 2009-243379.

*Primary Examiner* — Cris L Rodriguez
*Assistant Examiner* — Hao D Mai
(74) *Attorney, Agent, or Firm* — Wenderoth, Lind & Ponack, LLP.

(57) ABSTRACT

Artificial teeth are arranged in plates capable of being attached in an oral cavity as a dental prosthetic appliance, in which one or more linear arrangement direction indication parts showing the arrangement direction in the plates are provided on an occlusal plane of each of the molar teeth. At least one set of arrangement direction indication parts of the adjacent molar teeth is configured so as to extend generally in parallel direction. At least one set of arrangement direction indication parts of the antagonist upper molar teeth and lower molar teeth is configured so as to extend generally in parallel direction. The artificial molar teeth are arranged at an appropriate position according to the oral cavity environment of each patient, without requiring advanced skills and experiences, and are applicable to various arrangements of artificial teeth.

4 Claims, 8 Drawing Sheets

(56) References Cited

U.S. PATENT DOCUMENTS

| | | | | |
|---|---|---|---|---|
| 2,144,198 | A | 1/1939 | Page | |
| 2,219,559 | A * | 10/1940 | Lentz | 433/55 |
| 2,419,248 | A | 4/1947 | Blanchard | |
| 2,570,562 | A | 10/1951 | Kinsley | |
| 3,252,220 | A | 5/1966 | Goddard | |
| 3,755,898 | A | 9/1973 | Warren | |
| 3,959,881 | A * | 6/1976 | Kokal, Jr. | 433/70 |
| 4,194,288 | A | 3/1980 | Hass | |
| 4,650,417 | A * | 3/1987 | Schwartz | 433/196 |
| 4,659,311 | A * | 4/1987 | Raskin | 433/55 |
| 4,676,748 | A * | 6/1987 | Pietkivitch | 433/71 |
| 4,797,096 | A | 1/1989 | Ito et al. | |
| 4,906,186 | A * | 3/1990 | France, Jr. | 433/72 |
| 2,203,226 | A | 6/1990 | Klicka | |
| 5,049,075 | A | 9/1991 | Barrut | |
| 5,163,841 | A * | 11/1992 | Schreinemakers | 433/72 |
| 5,385,155 | A * | 1/1995 | Kittelsen et al. | 128/861 |
| 5,951,289 | A | 9/1999 | Kura et al. | |
| 5,954,503 | A * | 9/1999 | Skarky | 433/71 |
| 6,139,321 | A | 10/2000 | MacCulloch | |
| 6,231,339 | B1 * | 5/2001 | Skarky | 433/71 |
| 7,267,549 | B2 | 9/2007 | Monkmeyer | |
| 8,896,592 | B2 * | 11/2014 | Boltunov et al. | 345/419 |
| 2003/0091959 | A1 * | 5/2003 | Shinozaki et al. | 433/167 |
| 2004/0110110 | A1 | 6/2004 | Chishti et al. | |
| 2004/0137407 | A1 | 7/2004 | Lauciello | |
| 2008/0038696 | A1 * | 2/2008 | Raskin et al. | 433/214 |
| 2009/0233255 | A1 * | 9/2009 | De Souza Fonseca Silva et al. | 433/71 |
| 2010/0035208 | A1 * | 2/2010 | Kadobayashi | 433/191 |
| 2010/0040997 | A1 * | 2/2010 | Kadobayashi | 433/191 |
| 2010/0151419 | A1 * | 6/2010 | Kadobayashi et al. | 433/171 |
| 2010/0151422 | A1 * | 6/2010 | Kadobayashi et al. | 433/191 |
| 2010/0266988 | A1 * | 10/2010 | Satoh et al. | 433/197 |
| 2011/0045441 | A1 * | 2/2011 | Kadobayashi | 433/197 |
| 2011/0195373 | A1 * | 8/2011 | Waugh | 433/24 |
| 2012/0037166 | A1 | 2/2012 | Podmore et al. | 128/848 |

FOREIGN PATENT DOCUMENTS

| | | |
|---|---|---|
| JP | 2001-506525 | 5/2001 |
| JP | 2003-38525 | 2/2003 |
| WO | 2004/096077 | 11/2004 |

* cited by examiner

Fig.4

| | | Mesial buccal side | Distal buccal side | Mesial lingual side | Distal lingual side |
|---|---|---|---|---|---|
| Maxillary first premolar tooth | Buccal cusp | | | Posterior | Anterior |
| | Lingual cusp | | | Posterior | Anterior |
| Maxillary second premolar tooth | Buccal cusp | | | Posterior | Anterior |
| | Lingual cusp | | Balancing | Posterior | Anterior |
| Maxillary first molar tooth | MesialBuccal cusp | | | Posterior | Anterior |
| | DistalBuccal cusp | | | Posterior | Anterior |
| | MesialLingual cusp | | Balancing | Posterior | Anterior |
| | DistalLingual cusp | | Balancing | Posterior | Anterior |
| Maxillary second molar tooth | MesialBuccal cusp | | | Posterior | Anterior |
| | DistalBuccal cusp | | | Posterior | - |
| | MesialLingual cusp | | Balancing | Posterior | Anterior |
| | DistalLingual cusp | | Balancing | Posterior | - |
| Mandibular first premolar tooth | Buccal cusp | Anterior | Posterior | | |
| | Lingual cusp | - | - | | |
| Mandibular second premolar tooth | Buccal cusp | Anterior | Posterior | | Balancing |
| | Lingual cusp | Anterior | Posterior | | - |
| Mandibular first molar tooth | MesialBuccal cusp | Anterior | Posterior | | Balancing |
| | DistalBuccal cusp | Anterior | Posterior | | Balancing |
| | MesialLingual cusp | Anterior | Posterior | | - |
| | DistalLingual cusp | Anterior | Posterior | | - |
| Mandibular second molar tooth | MesialBuccal cusp | Anterior | Posterior | | Balancing |
| | DistalBuccal cusp | Anterior | Posterior | | Balancing |
| | MesialLingual cusp | Anterior | Posterior | | - |
| | DistalLingual cusp | Anterior | Posterior | | - |

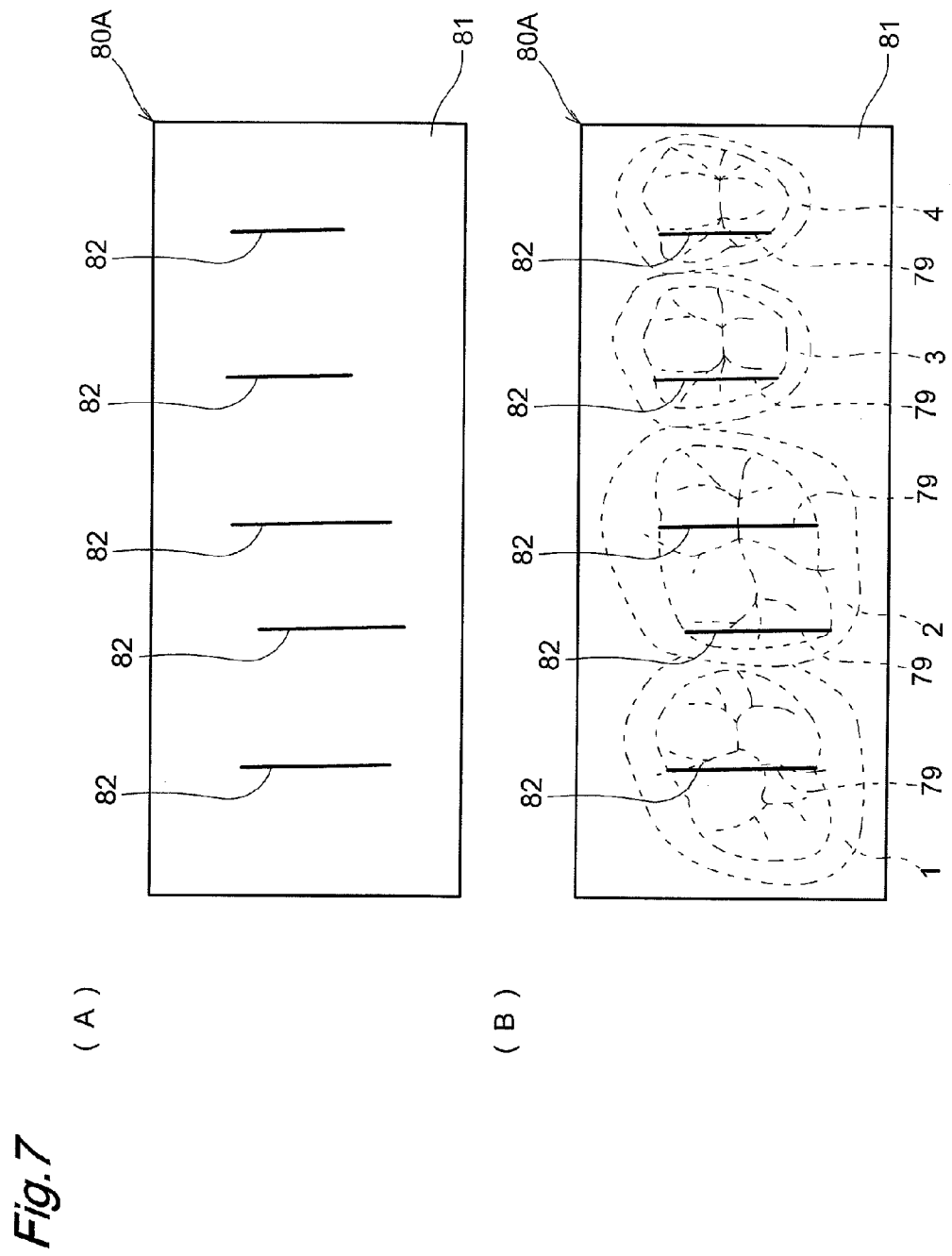

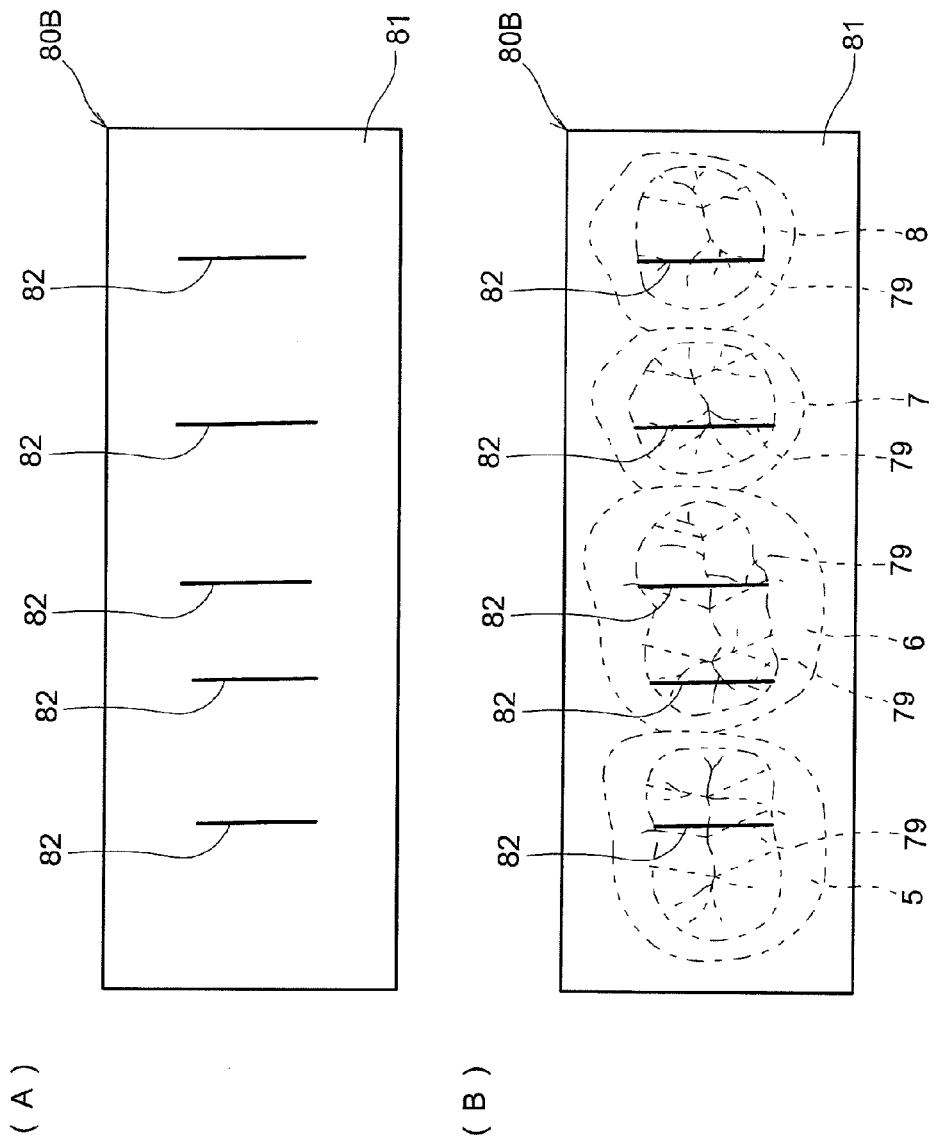

METHOD OF ARRANGING ARTIFICIAL MOLAR TEETH

BACKGROUND OF THE INVENTION

1. Field of the Invention

The present invention relates to artificial molar teeth which can be arranged easily when making a dental prosthetic appliance and are easy in mastication when wearing it as dentures.

2. Description of the Related Art

Arrangement of artificial molar teeth when making a dental prosthetic appliance required advanced skills and experiences. Therefore, it was difficult to arrange the artificial teeth in an appropriate positional relation. In particular, it was extremely difficult to arrange in a state as intended by the designer when designing the artificial teeth. Herein, the appropriate positional relation refers to a position where the function of the dentures can be fully exerted, and it is a state free from troubles in chewing, swallowing and eating food and speaking sound.

In the conventional artificial teeth, too much attention has been paid to natural teeth, and it was considered important to "copy" the natural teeth when making. To make stable dentures, it has been desired to arrange the adjacent artificial teeth easily. However, if made ideally in the designing stage of artificial teeth, a small error may be included in the fabricated artificial teeth. As a result, the artificial teeth may cause occlusal imbalance and disrupt arrangement and son on. In the conventional artificial teeth, accordingly, the surface state was largely changed by grinding largely after arrangement. It has been hence desired to develop artificial teeth easy in arrangement at proper positions and easy in adjustment, even if there are some defects in forming, in the arrangement of artificial teeth of upper and lower jaws.

PCT Application International Publication WO2004/096077 discloses artificial molar teeth, as artificial molar teeth for lingualized occlusion, in which all of four teeth including the maxillary or mandibular first premolar tooth, second premolar tooth, first molar tooth and second molar tooth are connected to each other. In these artificial molar teeth, a blade form is imparted to the lingual cusp of the upper molar teeth while protrusions are formed in the buccal cusp of the mandibular second premolar tooth and second molar tooth. The sliding gaps between these artificial molar teeth and the maxillary artificial molar teeth opposing thereto are demarcated, and a groove extending through the four teeth is formed at the basement side of these four connected artificial molar teeth. This groove has openings at the end of the first premolar tooth and the end of the second molar tooth.

However, PCT Application International Publication WO2004/096077 relates to connected teeth which are artificial molar teeth with a focus on masticatory function because the blade is provided in the lingual cusp of the maxillary artificial molar teeth, and the protrusion is formed in the buccal cusp of the second molar tooth. Moreover, because of the connected teeth, application in arrangement is poor, and it is not easy to arrange in each clinical case.

Japanese Unexamined Patent Publication No. 2003-38525 discloses an artificial tooth assembly having a maxillary portion and a mandibular portion. The maxillary portion includes a maxillary artificial tooth portion having maxillary artificial teeth, an upper side holding tool for holding the maxillary artificial tooth portion, and a bump portion as upper side positioning means provided in the upper side holding tool. Similarly, the mandibular portion includes a mandibular artificial tooth portion, a lower side holding tool, and a groove as lower side positioning means. The maxillary portion and the mandibular portion are positioned in an appropriate occlusal state when the maxillary artificial teeth and mandibular artificial teeth are engaged by the bump portion and the groove. The artificial tooth assembly having the above configuration lessens the working labor of planting of artificial teeth, and shortens the term for making the dentures in appropriate occlusal state, and enables the planting in a simple structure and easy process, without requiring troublesome and individual positioning operation, and without demanding any particular consideration on the appropriate occlusal state.

In Japanese Unexamined Patent Publication No. 2003-38525, however, since the artificial teeth are arranged by using the holding tool, it is difficult to apply to various arrangements of artificial teeth in individual clinical cases.

Japanese National Publication No. 2001-506525 (WO98/26728) discloses an artificial tooth arrangement device made of a flexible material, and having a tooth support ribbon molded so as to form an arch shape generally corresponding to the upper or lower natural dental arch. The artificial teeth are detachably mounted and arranged in a manner profiling the natural dental arch on the support ribbon so that the grooves of the teeth engage hooks of the ribbon.

However, the arrangement device of Japanese Unexamined Patent Publication No. 2001-506525 requires an arrangement jig, and it can be applied in making dentures of a full mouse, but otherwise it can be hardly applied in various artificial tooth arrangements in clinical cases.

SUMMARY OF THE INVENTION

It is an object of the invention to provide artificial molar teeth applicable to various artificial tooth arrangements, and capable of arranging at appropriate positions according to the oral cavity environment of each patient without requiring advanced skills and experiences.

To achieve the above object, the present invention is directed to artificial molar teeth arranged in plates attached in an oral cavity as a dental prosthetic appliance, wherein one or more linear arrangement direction indication parts showing the arrangement direction in the plates are provided on an occlusal plane of each of the molar teeth.

Specifically, these artificial molar teeth are artificial molar teeth including two or more molar teeth adjacently arranged in the mesiodistal direction in plates attached in an oral cavity as a dental prosthetic appliance, wherein one or more linear arrangement direction indication parts showing the arrangement direction in the plates are provided on an occlusal plane of each of the molar teeth, and at least one set of the arrangement direction indication parts in the adjacent molar teeth is extended generally in the parallel direction.

In the artificial molar teeth, since the arrangement direction indication parts showing the arrangement direction are provided in the occlusal plane, only by disposing so that the arrangement direction indication parts may be extended in a desired direction, it is possible to arrange securely in the specified direction. In other words, the molar teeth made according to various clinical cases can be arranged at appropriate positions in the mesiodistal direction and the buccal-lingual direction according to the oral cavity environment of each patient without requiring advanced skills and experiences.

In these artificial molar teeth, the arrangement direction indication parts are preferably formed of at least one of contour lines of contour parts, grooves formed between the adjacent contour parts, and lines formed by coloring.

Of the upper molar teeth and the lower molar teeth, when one of the arrangement direction indication parts is formed of the contour line of the contour part, and other arrangement direction indication part is made of the groove formed between the adjacent contour parts, it is preferable to configure so that the contour part may not be fitted into the groove with the upper molar teeth and the lower molar teeth matched in the central occlusion position. As a result, after making the dentures, the escaping space for food is assured, and it is easy to chew, and the cutting function and the grinding function may be added.

The arrangement direction indication parts are preferably provided so as to extend in the sideways motion direction of the motion side. Thus, the arrangement direction indication parts are extended in the sliding direction when starting motion from the chewing position or resting position, and the function of chewing, cutting, and grinding may be enhanced.

Alternatively, the arrangement direction indication parts are preferably provided so as to extend in the mesiodistal direction. Thus, similarly to the above, the arrangement direction may be determined easily. In this case, the arrangement direction indication parts of the molar teeth adjacent in an occlusal plane view are preferably positioned linearly. Thus, the arrangement work may be further enhanced in efficiency.

Alternatively, the arrangement direction indication parts are preferably provided so as to extend in the buccal-lingual direction. Thus, the arrangement direction may be determined easily.

In these artificial molar teeth, in order to confirm the arrangement state of artificial molar teeth having linear arrangement direction indication parts provided on occlusal planes in at least one position or more showing the arrangement direction in plates, it is preferable to provide an arrangement confirmation sheet in which confirm lines overlapping with the arrangement direction indication parts in the normal arrangement state are provided in a base sheet through which the back side can be seen.

Thus, with the molar teeth arranged in the plates, only by disposing the arrangement confirmation sheet on the occlusal plane, it can be easily checked whether or not the arrangement is in the normal state in the mesiodistal direction and the buccal-lingual direction. If there is an error in arrangement, it is possible to adjust easily. Hence, the molar teeth may be arranged easily without requiring advance skills and experiences.

According to the artificial teeth of the invention, since the arrangement direction indication parts showing the arrangement direction are provided in the occlusal plane, the teeth can be arranged securely in a specified direction. That is, the molar teeth made according to various clinical cases can be arranged at proper positions according to the oral cavity environment of each patient without requiring advanced skills and experiences.

BRIEF DESCRIPTION OF THE DRAWINGS

Further objects and advantages of the present invention will become clear from the following description taken in conjunction with the preferred embodiments thereof with reference to the accompanying drawings, in which:

FIG. 4 is a table showing occlusal facets formed on the cusps of the molar teeth;

FIGS. 7A and 7B are plan views each showing an arrangement confirmation method of upper molar teeth in the third embodiment; and FIGS. 8A and 8B are plan views each showing an arrangement confirmation method of lower molar teeth in the third embodiment.

DESCRIPTION OF THE PREFERRED EMBODIMENTS

An embodiment of the present invention is described in detail below with reference to the accompanying drawings.

The present invention relates to techniques of making artificial teeth as a dental prosthetic appliance of denture, especially relating to techniques of making artificial molar teeth. The artificial molar teeth include a first molar tooth, a second molar tooth, a first premolar tooth, and a second premolar tooth, and two or more adjacent teeth thereof may be combined, and more preferably all four adjacent teeth may combined. Moreover, four teeth including upper and lower mutually opposing antagonist first molar teeth, antagonist second molar teeth, antagonist first premolar teeth, and antagonist second premolar teeth are preferred, and more preferably eight teeth of all upper and lower opposing molar teeth may be combined.

Figure 1:
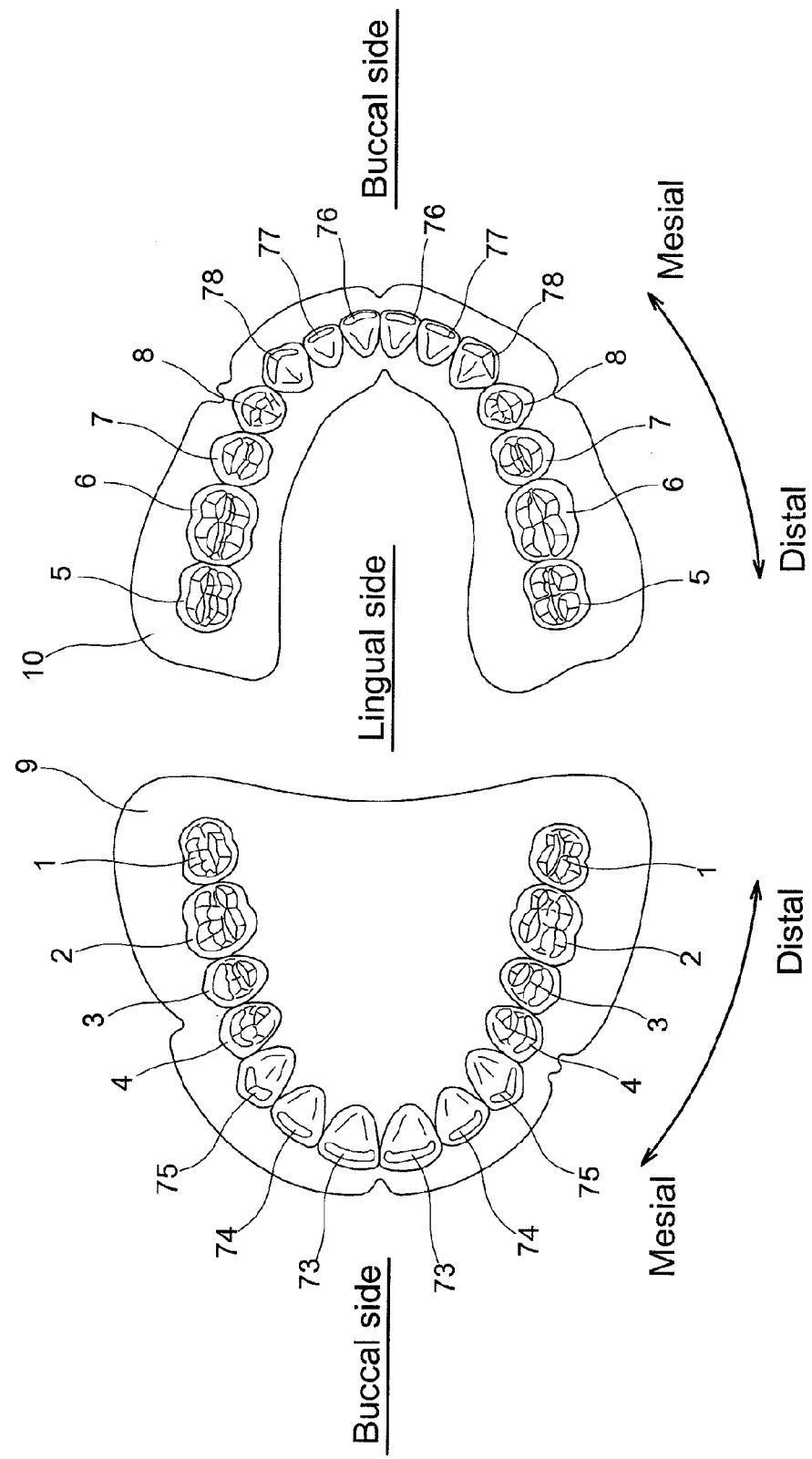
FIG. 1 is a plan view showing a basic configuration of artificial molar teeth to be arranged in the upper jaw and lower jaw.

FIG. 1 shows an arrangement of all artificial teeth, in which the left side shows the upper jaw, and the right side shows the lower jaw. In the artificial teeth, one upper tooth corresponds to one lower tooth (tooth-to-tooth). In the following description, the direction approaching anterior teeth refers to a mesial side, and an opposite departing direction is a distal side. In an oral cavity, the inward direction is a lingual side, and the outward direction is a buccal side. The occlusal side of teeth is a cuspal side, and a tooth root side is a cervical side.

Figure 2:
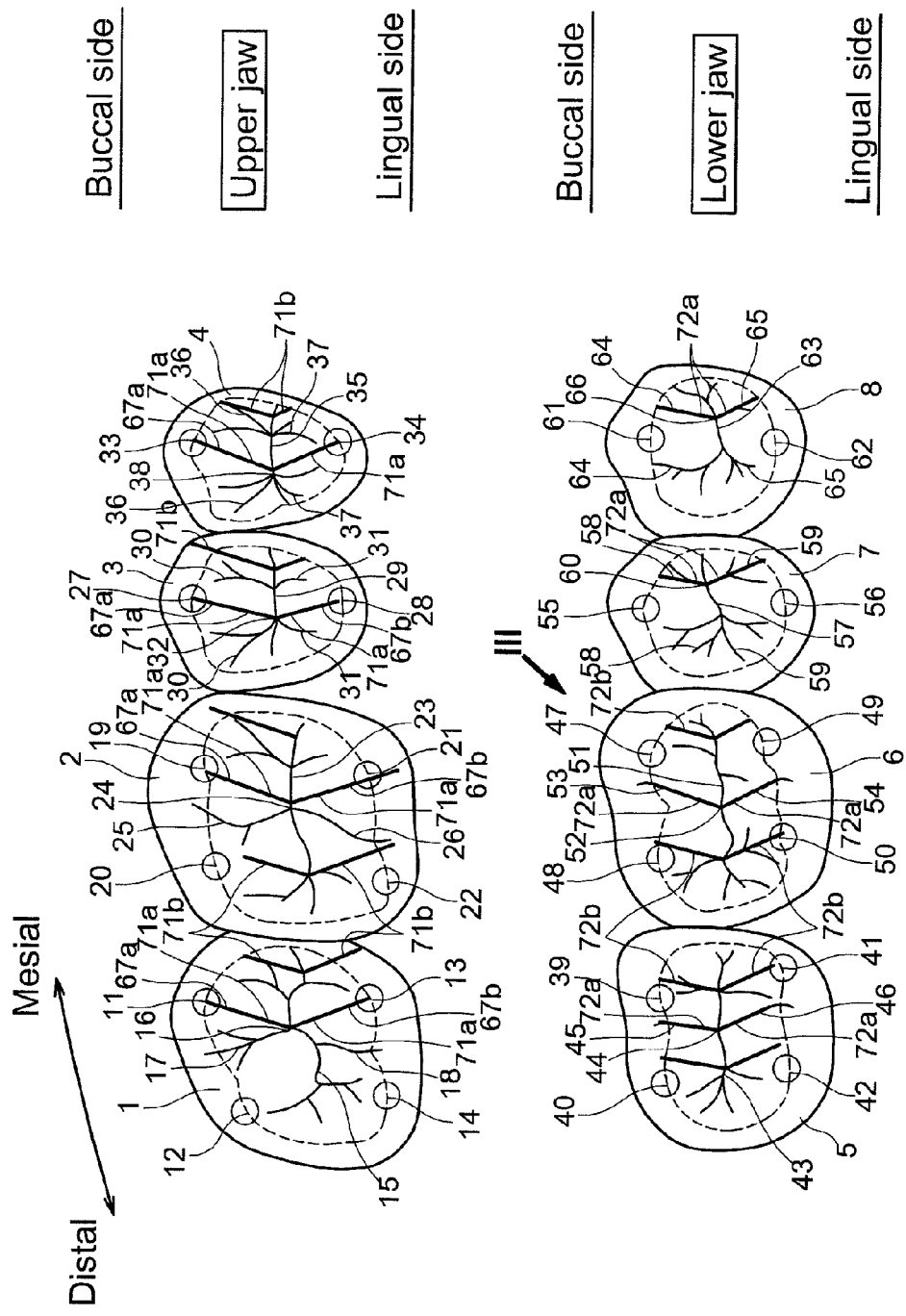
FIG. 2 is a plan view of upper molar teeth and lower molar teeth in a first embodiment.

FIG. 2 shows the arrangement of upper molar teeth 1 to 4 and lower molar teeth 5 to 8 of the embodiment arranged on the plates 9, 10 as seen from the maxillary direction. The upper side is a view of the upper molar teeth 1 to 4 as seen from the maxillary direction, and the lower side is a view of the lower molar teeth 5 to 8 as seen from the maxillary direction. However, since the occlusion state of the upper molar teeth 1 to 4 is not known when seen from the maxillary direction, in order to show the state of occlusion, the occlusal plane as seen from above is shown. In the figure, the circle (O) mark shows the cusp tip of each cusp. The broken line in FIG. 2 shows the ridge of the molar teeth 1 to 8, and its inner side is the cuspal plane and the outer side is the outer circumference.

As shown in the figure, the artificial molar teeth of the embodiment include a maxillary second molar tooth 1, a maxillary first molar tooth 2, a maxillary second premolar tooth 3, and a maxillary first premolar tooth 4 arranged in the upper jaw, and a mandibular second molar tooth 5, a mandibular first molar tooth 6, a mandibular second premolar tooth 7, and a mandibular first premolar tooth 8 arranged in the lower jaw opposing thereto. The upper molar teeth 1 to 4 are arranged in the maxillary plate 9, and the lower molar teeth 5 to 8 are arranged in the mandibular plate 10, and by way of these plates 9, 10, the teeth are detachably arranged in the oral cavity of the patient. The mandibular plate 10 has a generally U-shape in order to expose the tongue of the patient.

The maxillary second molar tooth 1 is provided with a mesial buccal cusp 11 at the mesial side of the buccal side, a distal buccal cusp 12 at the distal side of the buccal side, a mesial lingual cusp 13 at the mesial side of the lingual side, and a distal lingual cusp 14 at the distal side of the lingual side. These cusps 11 to 14 are lumps of tooth substance formed in a shape raised like a taper. The maxillary second molar tooth 1 has a central groove 15 extending in the mesiodistal direction formed between each pair of the buccal cusps 11, 12 and the lingual cusps 13, 14. At a specified position on the central groove 15, a fossa 16 is formed, which reaches the maximum depth in the vertical direction in the arranged state. The maxillary second molar tooth 1 is also provided with a buccal groove 17 and a lingual groove 18 provided between each pair of the mesial cusps 11, 13, and the distal cusps 12, 14. These side grooves 17, 18 are large grooves extending from the central groove 15 and the fossa 16 to the buccal face and the lingual face, and they are extended from the cuspal side on the cervical side at the buccal face and the lingual face.

The maxillary first molar tooth 2 is provided with a mesial buccal cusp 19 at the mesial side of the buccal side, a distal buccal cusp 20 at the distal side of the buccal side, a mesial lingual cusp 21 at the mesial side of the lingual side, and a distal lingual cusp 22 at the distal side of the lingual side. These cusps 19 to 22 are lumps of tooth substance formed in a shape raised like a taper. The maxillary first molar tooth 2 has a central groove 23 extending in the mesiodistal direction formed between each pair of the buccal cusps 19, 20 and the lingual cusps 21, 22, and at a specified position on the central groove 23, a fossa 24 is formed. Further, the maxillary first molar tooth 2 is also provided with a buccal groove 25 and a lingual groove 26, as in the maxillary second molar tooth 1, formed between each pair of the mesial cusps 19, 21, and the distal cusps 20, 22.

The maxillary second premolar tooth 3 is provided with one buccal cusp 27 at the buccal side, and one lingual cusp 28 at the lingual side. These cusps 27 and 28 are lumps of tooth substance formed in a shape raised like a taper. The maxillary second premolar tooth 3 has a central groove 29 extending in the mesiodistal direction formed between the buccal cusps 27, 28. At both ends of the central groove 29, further, a buccal supplemental groove 30 and a lingual supplemental groove 31 are formed respectively so as to extend to the buccal side and the lingual side. A fossa 32 is formed at the intersection of the central groove 29 and the supplemental grooves 30, 31.

The maxillary first premolar tooth 4 is provided with one buccal cusp 33 at the buccal side, and one lingual cusp 34 at the lingual side. These cusps 33 and 34 are lumps of tooth substance formed in a shape raised like a taper. The maxillary first premolar tooth 4 has a central groove 35 extending in the mesiodistal direction formed between the buccal cusps 33, 34, and at both ends of the central groove 35, further, a buccal supplemental groove 36 and a lingual supplemental groove 37 are formed. A fossa 38 is formed at the intersection of the central groove 35 and the supplemental grooves 36, 37.

On the other hand, the mandibular second molar tooth 5 is provided with a mesial buccal cusp 39 at the mesial side of the buccal side, a distal buccal cusp 40 at the distal side of the buccal side, a mesial lingual cusp 41 at the mesial side of the lingual side, and a distal lingual cusp 42 at the distal side of the lingual side. These cusps 39 to 42 are lumps of tooth substance formed in a shape raised like a taper. The mandibular second molar tooth 5 has a central groove 43 extending in the mesiodistal direction formed between each pair of the buccal cusps 39, 40 and the lingual cusps 41, 42, and a fossa 44 is formed at a specified position on the central groove 43. The mandibular second molar tooth 5 is also provided with a buccal groove 45 and a lingual groove 46 provided between each pair of the mesial cusps 39, 41, and the distal cusps 40, 42, like the maxillary molar teeth 1, 2.

The mandibular first molar tooth 6 is provided with a mesial buccal cusp 47 at the mesial side of the buccal side, a distal buccal cusp 48 at the distal side of the buccal side, a mesial lingual cusp 49 at the mesial side of the lingual side, and a distal lingual cusp 50 at the distal side of the lingual side. The mandibular first molar tooth 6 may be also provided with another cusp at the distal side. These cusps 47 to 50 are lumps of tooth substance formed in a shape raised like a taper. The mandibular first molar tooth 6 has a central groove 51 extending in the mesiodistal direction formed between each pair of the buccal cusps 47, 48 and the lingual cusps 49, 50, and at a specified position on the central groove 51, a fossa 52 is formed. Further, the mandibular first molar tooth 6 is also provided with a buccal groove 53 and a lingual groove 54, as in the molar teeth 1, 2, 5, formed between each pair of the mesial cusps 47, 49, and the distal cusps 48, 50.

The mandibular second premolar tooth 7 is provided with one buccal cusp 55 at the buccal side, and one lingual cusp 56 at the lingual side. These cusps 55 and 56 are lumps of tooth substance formed in a shape raised like a taper. The mandibular second premolar tooth 7 has a central groove 57 extending in the mesiodistal direction formed between the buccal cusps 55, 56, and at both ends of the central groove 57, further, a buccal supplemental groove 58 and a lingual supplemental groove 59 are formed. A fossa 60 is formed at the intersection of the central groove 57 and the supplemental grooves 58, 59.

The mandibular first premolar tooth 8 is provided with one buccal cusp 61 at the buccal side, and one lingual cusp 62 at the lingual side. These cusps 61 and 62 are lumps of tooth substance formed in a shape raised like a taper. The mandibular first premolar tooth 8 has a central groove 63 extending in the mesiodistal direction formed between the buccal cusps 61, 62, and at both ends of the central groove 63, further, a buccal supplemental groove 64 and a lingual supplemental groove 65 are formed. A fossa 66 is formed at the intersection of the central groove 63 and the supplemental grooves 64, 65.

Of these upper molar teeth 1 to 4 and the lower molar teeth 5 to 8, the premolar teeth 3, 4, 7, 8 are not provided with buccal grooves 17, 25, 45, 53, and lingual grooves 18, 26, 46, 54, as in the molar teeth 1, 2, 5, 6. However, when the pair of premolar teeth 3, 4, and 7, 8 are formed as connected teeth, lateral grooves such as lingual grooves and buccal grooves are formed the connection portions.

In these molar teeth 1 to 8, sequentially from the distal side, the maxillary second molar tooth 1 and the mandibular second molar tooth 5 pair up and are engaged with each other, the maxillary first molar tooth 2 and the mandibular first molar tooth 6 pair up and are engaged with each other, the maxillary second premolar tooth 3 and the mandibular second premolar tooth 7 pair up and are engaged with each other, and the maxillary first premolar tooth 4 and the mandibular first premolar tooth 8 pair up and are engaged with each other. The specified cusps of these maxillary molar teeth 1 to 4 and the lower molar teeth 5 to 8 are engaged with the fossa of the antagonist molar teeth 5 to 8, 1 to 4, or the space of the adjacent antagonist molar teeth 5 to 8, 1 to 4 at the central occlusion position.

More specifically, the mesial lingual cusp 13 of the maxillary second molar tooth 1 is engaged with the fossa 44 of the mandibular second molar tooth 5, the distal lingual cusp 22 of the maxillary first molar tooth 2 is engaged with the space between the mandibular second molar tooth 5 and the mandibular first molar tooth 6, the mesial lingual cusp 21 of the maxillary first molar tooth 2 is engaged with the fossa 52 of the mandibular first molar tooth 6, the lingual cusp 28 of the maxillary second molar tooth 3 is engaged with the space between the mandibular first molar tooth 6 and the mandibular second premolar tooth 7, and the lingual cusp 34 of the maxillary first premolar tooth 4 is engaged with the space between the mandibular second premolar tooth 7 and the mandibular first premolar tooth 8. Further, the distal buccal cusp 40 of the mandibular second molar tooth 5 is engaged with the fossa 16 of the maxillary second molar tooth 1, the mesial buccal cusp 39 of the mandibular second molar tooth 5 is engaged with the space between the maxillary second molar tooth 1 and the maxillary first molar tooth 2, the distal buccal cusp 48 of the mandibular first molar tooth 6 is engaged with the fossa 24 of the maxillary first molar tooth 2, the mesial buccal cusp 47 of the mandibular first molar tooth 6 is engaged with the space between the maxillary first molar tooth 2 and the maxillary second premolar tooth 3, and the buccal cusp 55 of the mandibular second premolar tooth 7 is engaged with the space between the maxillary second premolar tooth 3 and the maxillary first premolar tooth 4. The engagement of the cusp with the space means that the entire cusp is engaged with a concave space, and that the cusp top is contacting with any one groove of the adjacent molar teeth 1 to 4, 5 to 8. The engagement of the cusp with the fossa includes the state of the cusp top contacting with the groove near the fossa.

In the upper molar teeth 1 to 4 and the lower molar teeth 5 to 8 in the embodiment, linear arrangement direction indication parts for instructing the arrangement direction in the plates 9, 10 are provided. These arrangement direction indication parts are mainly made of contour lines 67a of contour parts provided by forming the cusps in the molar teeth 1 to 8, and grooves formed between adjacent contour parts. In the location where contour lines 67a by contour parts cannot be formed, the arrangement direction indication parts are formed by indication grooves 67b intentionally provided so as to have a dent.

Figure 3:
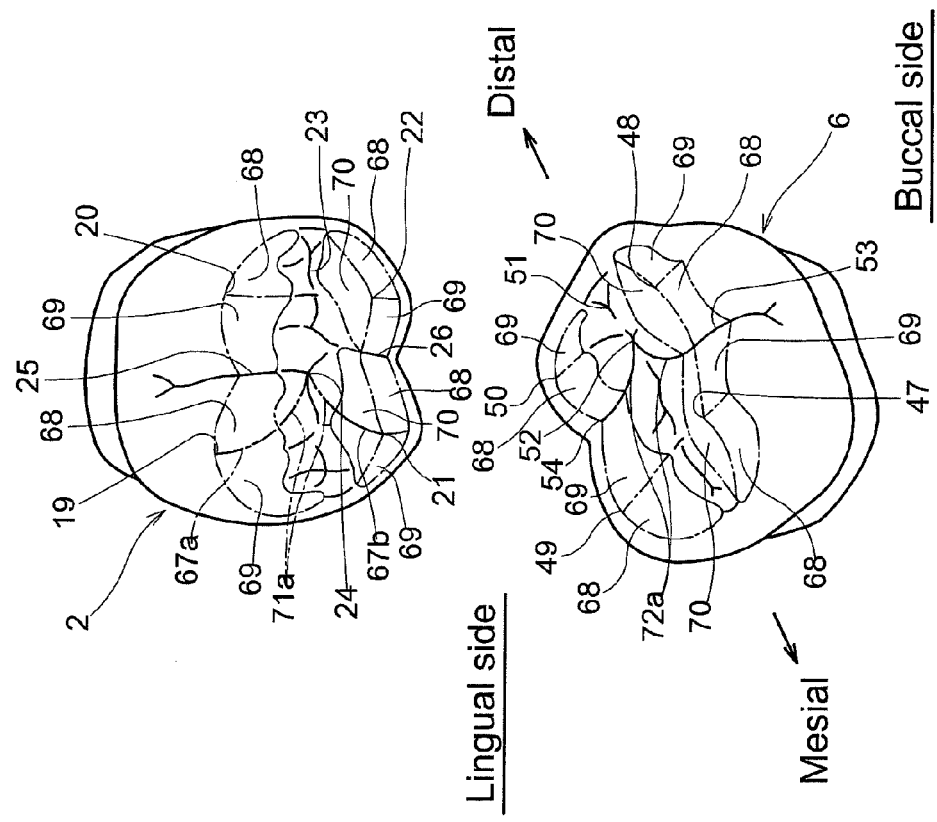
FIG. 3 is a perspective view showing a basic configuration for forming contour parts and grooves.

A basic configuration of the contour lines 67a of the contour parts and the grooves between the contour parts for composing the arrangement direction indication parts is described by referring to FIG. 3 and FIG. 4 showing the first molar teeth 2, 6. FIG. 3 is a view of FIG. 2 as seen from arrow III direction.

The contour lines 67a of the contour parts and the grooves between the contour parts are formed by occlusal facets 68 to 70 formed around the cusps of the molar teeth 1 to 8. These occlusal facets 68 to 70 come into slide contact with the occlusal facets 68 to 70 of the cusps of the antagonist when the lower jaw is moved in the forward motion, lateral motion, or intermediate motion.

As shown in FIG. 4, the distal lingual side of each cusp of the upper molar teeth 1 to 4, and the mesial buccal side of each cusp of the lower molar teeth 5 to 8 are provided with anterior occlusal facets 68 involved in the balancing function and the chewing function in lateral motion or intermediate motion. The anterior occlusal facet 68 is not formed on the distal cusps 12, 14 of the maxillary second molar tooth 1 and on the lingual cusp 62 of the mandibular first premolar tooth 8, because any sliding occlusal plane is not present in relation to the occlusion position.

Further, the mesial lingual side of each cusp of the upper molar teeth 1 to 4, and the distal buccal side of each cusp of the lower molar teeth 5 to 8 are provided with posterior occlusal facets 69 involved in the chewing function in lateral motion or backward motion. The posterior occlusal facet 69 is not formed on the lingual cusp 62 of the mandibular first premolar tooth 8, because any sliding occlusal plane is not present in relation to the occlusion position.

Moreover, the buccal side of lingual cusp of the upper molar teeth 1 to 3, and the lingual side of the buccal cusp of the lower molar teeth 5 to 7 are provided with balancing occlusal facets 70 involved in the balancing function in lateral motion or backward motion. This balancing occlusal facet 70, together with the anterior occlusal facet 68 and the posterior occlusal facet 69, forms a shape of triangular pyramid. The balancing occlusal facet 70 is not formed on the lingual cusp 34 of the maxillary first premolar tooth 4, and on the buccal cusp 61 of the mandibular first premolar tooth 8, because any sliding occlusal plane is not present in relation to the occlusion position.

As shown in FIG. 3, the contour part is formed so as to rise from the occlusal plane like an almond, by the curvature of the occlusal facets 68 to 70. The contour part has a contour line 67a formed in the most contour ridge part (boundary part), depending on the difference of the curvature of the occlusal facets 68 to 70. The contour line 67a may be formed of corners formed by intersection of the occlusal facets 68 to 70, and may be preferably formed of tops of the curved surfaces. The buccal grooves 25, 53 and the lingual grooves 26, 54 are formed of linear dents formed in the boundary area of a contour part and other contour part. These buccal grooves 25, 53 and the lingual grooves 26, 54 are formed between the anterior occlusal facet 68 and the posterior occlusal facet 69 adjacent to each other in the mesiodistal direction.

In the upper molar teeth 1 to 4 of the embodiment, as one of the arrangement direction indication parts, the contour line 67a of the contour part formed at the buccal side is formed to extend linearly from the start point of the fossae 16, 24, 32, 38 to the mesial side at specified angle in a occlusal plan view. However, at the buccal side of the lingual cusps 13, 14, 21, 22, 28 of the upper molar teeth 1 to 3 excluding the maxillary first premolar tooth 4, since the balancing occlusal facet 70 is formed, the contour line 67a cannot be formed. Accordingly, in the balancing occlusal facet 70 formed in these upper molar teeth 1 to 3, an indication groove 67b is formed as being extended linearly from the start point of the fossae 16, 24, 32, to the mesial side at a specified angle. The balancing occlusal facet 70 is not formed at the buccal side of the lingual cusp 34 of the maxillary first premolar tooth 4, and the occlusal facets 68, 69 are not formed in this position. Similarly, since the occlusal facets 68, 69, 70 are formed around the cusp, the contour line 67a for forming the cusp is not formed near the fossae 16, 24, 32, 38. Accordingly, in the embodiment, an auxiliary contour part is provided at the buccal side of the lingual cusp 34 of the maxillary first premolar tooth 4, and an auxiliary contour line 71a of this auxiliary contour part is formed to extend linearly from the start point of the fossa 38 to the distal side at a specified angle in a occlusal plane view. Similarly, near the fossae 16, 24, 32 of the molar teeth 1 to 3, an auxiliary contour part is provided to be continuous to the contour line 67a and the indication groove 67b, and a part of the arrangement direction indication part is formed by the auxiliary contour line 71a of this auxiliary contour part.

In the lower molar teeth 5 to 8 of the embodiment, as the arrangement direction indication parts, buccal grooves 45, 53, buccal supplemental grooves 58, 64, and lingual grooves 46, 54, lingual supplemental grooves 59, 65 are formed to extend linearly from the start point of the fossae 44, 52, 60, 66 to the mesial side at specified angle in a occlusal plan view. However, since the occlusal facets 68, 69, 70 are formed around the cusp, substantially, near the fossae 44, 52, 60, 66, grooves 45, 53, 58, 64, 46, 54, 59, 65 are not extended. Accordingly, in the embodiment, near the fossae 44, 52, 60, 66, an auxiliary groove 72a by a pair of auxiliary contour parts is formed so as to be continuous to each groove, and together with this auxiliary groove 72a, the arrangement direction instruction part is formed.

At the buccal side of the upper molar teeth 1 to 4, the arrangement direction indication parts formed of contour lines 67a, 71a of the contour parts are extended parallel to each other in an occlusal plane view in the arranged state in the maxillary plate 9. At the lingual side of the upper molar teeth 1 to 4, the arrangement direction indication parts formed of indication groove 67b and contour line 71a are extended parallel to each other in an occlusal plane view in the arranged state in the maxillary plate 9. Similarly, at the buccal side of the lower molar teeth 5 to 8, the arrangement direction indication parts formed of buccal grooves 45, 53, buccal supplemental grooves 58, 64 and auxiliary grooves 72a are extended parallel to each other in an occlusal plane view in the arranged state in the mandibular plate 10. At the lingual side of the lower molar teeth 5 to 8, the arrangement direction indication parts formed of lingual grooves 46, 54, lingual supplemental grooves 59, 65 and auxiliary grooves 72a are extended parallel to each other in an occlusal plane view in the arranged state in the mandibular plate 10. Accordingly, in the antagonist upper molar teeth 1 to 4 and lower molar teeth 5 to 8, the arrangement indication parts are extended in parallel in the arranged state in the plates 9, 10. Hence, the arrangement indication parts formed of the contour lines 67a, 71a of the upper molar teeth 1 to 4, and the arrangement indication parts formed of grooves 45, 53, 58, 64, 72a of the lower molar teeth 5 to 8 do not occlude with each other when joined at the central occlusion position. As a result, the escaping route for food is assured, and easy chewing is guaranteed, and in addition to the cutting function, the grinding function can be added.

The extending direction of the contour lines 67a, 71a and the grooves 45, 46, 53, 54, 58, 59, 64, 65 in the first embodiment is formed to be extended in the motion direction of the molar teeth 1 to 4, 5 to 8. The motion direction is the sliding direction of the opposite molar teeth 1 to 4, 5 to 8, that is, the lateral motion direction of moving when in action from the chewing position or rest position. This direction is important when making dentures, and the teeth must be arranged while paying attention to the lateral moving direction of the motion side. In this sense of meaning, the dental technician must be always conscious of the direction, and the arrangement carries out easily when the direction of the generally parallel contour parts or grooves is in the lateral motion direction of the motion side.

The lateral motion of the working side refers to the motion of the upper molar teeth 1 to 4 moving to the lingual side with respect to the lower molar teeth 5 to 8. The lateral motion of the balancing side refers to the motion of the upper molar teeth 1 to 4 moving to the buccal side with respect to the lower molar teeth 5 to 8. From these motions, contact marks are left over in the lingual direction from the portions of the fossae 44, 52, 60, 66 of the lower molar teeth 5 to 8 at the working side, and contact marks are left over in the buccal direction from the portions of the fossae 44, 52, 60, 66 of the lower molar teeth 5 to 8 at the balancing side. When the upper jaw is described, contact marks are left over in the buccal direction from the portions of the fossae 16, 24, 32, 38 of the upper molar teeth 1 to 4 at the working side, and contact marks are left over in the lingual direction from the portions of the fossae 16, 24, 32, 38 of the upper molar teeth 1 to 4 at the balancing side.

In the embodiment, as shown in FIG. 2, the upper molar teeth 1 to 4 are provided with not only contour lines 67a, 71a as arrangement direction indication parts extending from the fossae 16, 24, 32, 38, but also auxiliary contour lines 71b from the central grooves 15, 23, 29, 35 so as to extend in parallel thereto. Similarly, the lower molar teeth 5, 6 are provided with not only lateral grooves 45, 46, 53, 54 extending from the fossae 44, 52, but also auxiliary grooves 72b from the central grooves 43, 51 so as to extend in parallel thereto. The supplemental grooves 58, 59, 64, 65 positioned at the distal side of the lower premolar teeth 7, 8 are inclined and extended oppositely to the mesial side supplemental grooves 58, 59, 64, 65 as arrangement direction indication parts, and cannot be used commonly as the arrangement direction indication parts, and they are not formed linearly. In other words, all contour lines and grooves are not formed and extended in parallel, but are formed at least in one position or more. However, when contour lines and grooves are at two or more positions as arrangement direction indication parts, preferably, they are positioned generally uniformly in the mesiodistal direction when they are observed three-dimensionally.

Next, a description is given of an operation of arranging these molar teeth 1 to 8 in the plates 9, 10. In the completed dentures, the plates 9, 10 are made of resin. The resin-made plates 9, 10 are formed in place of the wax rims as temporary plates after arrangement of artificial teeth. More specifically, the wax rims are made of wax as temporary plates from patterns taken from a patient, and the artificial teeth are arranged in the wax rims to make temporary dentures. The temporary dentures are covered with plaster, and the wax rim is melted away, and the resin is injected, so that resin-made plates 9, 10 are formed, and the completed dentures are taken out from the plaster. The arrangement state in the plates 9, 10 includes both a state of arrangement in a complete resin plates, and a state of arrangement in temporary wax plates.

First, in the mandibular plate 9 provided with an upper central incisor 73, an upper lateral incisor 74, and an upper canine 75, the maxillary first premolar tooth 4 is arranged. At this time, the positions of the tops of the cusps 33, 34 of the maxillary first premolar tooth 4 in the buccal-lingual direction and the apical-cervical direction is arranged to correspond to the apex of the upper canine 75.

Next, the maxillary second premolar tooth 3 is arranged in the maxillary plate 9. At this time, the positions of the cusps 27, 28 of the maxillary second premolar tooth 3 in the buccal-lingual direction and the cuspal-cervical direction are arranged to correspond to the cusps 33, 34 of the maxillary first premolar tooth 4. The contour lines 67a, 71a and the indication grooves 67b as the arrangement direction indication parts, are adjusted to be parallel to the contour lines 67a, 71a and the indication grooves 67b as the arrangement position indication parts of the previously arranged maxillary first premolar tooth 4.

Next, the maxillary first molar tooth 2 is arranged in the maxillary plate 9. At this time, the positions of the buccal cusps 19, 20 and the lingual cusps 21, 22 of the maxillary first molar tooth 2 in the buccal-lingual direction and the cuspal-cervical direction are arranged to correspond to the buccal cusp 27 and the lingual cusp 28 of the maxillary second premolar tooth 3. The contour lines 67a, 71a and the indication grooves 67b as the arrangement direction indication parts are adjusted to be parallel to the contour lines 67a, 71a and the indication grooves 67b as the arrangement position indication parts of the previously arranged maxillary second premolar tooth 3.

Next, the maxillary second molar tooth 1 is arranged in the maxillary plate 9. At this time, the positions of the buccal cusps 11, 12 and the lingual cusps 13, 14 of the maxillary second molar tooth 1 in the buccal-lingual direction and the cuspal-cervical direction are arranged to correspond to the buccal cusps 19, 20 and the lingual cusps 21, 22 of the maxillary first molar tooth 2. The contour lines 67a, 71a and the indication grooves 67b as the arrangement direction indication parts are adjusted to be parallel to the contour lines 67a, 71a and the indication grooves 67b as the arrangement position indication parts of the previously arranged maxillary first molar tooth 2.

Similarly, in the mandibular plate 10 having the lower central incisor 76, the lower lateral incisor 77, and the lower canine 78, the mandibular first premolar tooth 8 is arranged at the distal side of the lower canine 78. At this time, the positions of the peaks of the cusps 61, 62 of the mandibular first premolar tooth 8 in the buccal-lingual direction and the apical-cervical direction are arranged to correspond to the apex of the lower canine 78.

The mandibular second premolar tooth 7 is arranged in the mandibular plate 10. At this time, the positions of the cusps 55, 56 of the mandibular second premolar tooth 7 in the buccal-lingual direction are arranged to correspond to the cusps 61, 62 of the mandibular first premolar tooth 8. The buccal supplemental groove 58 and the lingual supplemental groove 59 as the arrangement direction indication parts are adjusted to be parallel to the buccal supplemental groove 64 and the lingual supplemental groove 65 as the arrangement position indication parts of the previously arranged mandibular first premolar tooth 8.

Next, the mandibular first molar tooth 6 is arranged in the mandibular plate 10. At this time, the positions of the buccal cusps 47, 48 and the lingual cusps 49, 50 of the mandibular first molar tooth 6 in the buccal-lingual direction and the cuspal-cervical direction are arranged to correspond to the buccal cusp 55 and the lingual cusp 56 of the mandibular second premolar tooth 7. As the arrangement direction indication parts, the buccal groove 53, the lingual groove 54, an the auxiliary grooves 72a, 72b are adjusted to be parallel to the buccal supplemental groove 58 and the lingual supplemental groove 59 as the arrangement position indication parts of the previously arranged mandibular second premolar tooth 7.

Finally, the mandibular second molar tooth 5 is arranged in the mandibular plate 10. At this time, the positions of the buccal cusps 39, 40 and the lingual cusps 41, 42 of the mandibular second molar tooth 5 in the buccal-lingual direction and the cuspal-cervical direction are arranged to correspond to the buccal cusps 47, 48 and the lingual cusps 49, 50 of the mandibular first molar tooth 6. The buccal groove 45, the lingual groove 46, an the auxiliary grooves 72a, 72b as the arrangement direction indication parts are adjusted to be parallel to the buccal groove 53, the lingual groove 54, and the auxiliary grooves 72a, 72b as the arrangement position indication parts of the previously arranged mandibular first molar tooth 6.

Thus, in the invention, parts of the contour lines 67a formed in the upper molar teeth 1 to 4, and the buccal grooves 45, 53, 58, 64 and the lingual grooves 46, 54, 59, 65 formed in the lower molar teeth 5 to 8 are composed as arrangement direction indication parts.

Accordingly, only by arranging them so as to extend in parallel, the molar teeth 1 to 4, 5 to 8 adjacent in the mesiodistal direction may be arranged easily and securely in a specified directivity.

Accordingly, when arranging the upper molar teeth 1 to 4 and lower molar teeth 5 to 8 in the maxillary plate 9 and the mandibular plate 10, without requiring advanced skills and experiences, the teeth can be arranged at appropriate positions according to the oral cavity environment of each patient. That is, the oral cavity of patient is very large in individual difference, and in clinical cases of edentulous jaw, the space, the alveolar ridge height, and angle in the oval cavity are largely different, and in such varied clinical cases, the artificial molar teeth can be arranged easily and in a short time, and the situation in the oral cavity can be reproduced. Besides, since the artificial teeth are arranged on the wax rim, it has been previously difficult to understand the positional relation of mutual artificial teeth, but the situation can be understood easily. In addition, since the correct arrangement position of the molar teeth 1 to 8 can be easily determined, the arrangement working efficiency is notably enhanced. Moreover, when the prosthetic appliance is attached, the aesthetic appearance in the oral cavity is enhanced.

In the embodiment, the contour lines and the grooves for forming the arrangement direction indication parts are provided to be extended in the sideward motion direction, that is, the sliding direction when motion is started from the chewing position or rest position. Accordingly, after making the dentures, easy chewing is guaranteed and in addition to cutting function, the grinding function is enhanced.

Figure 5:
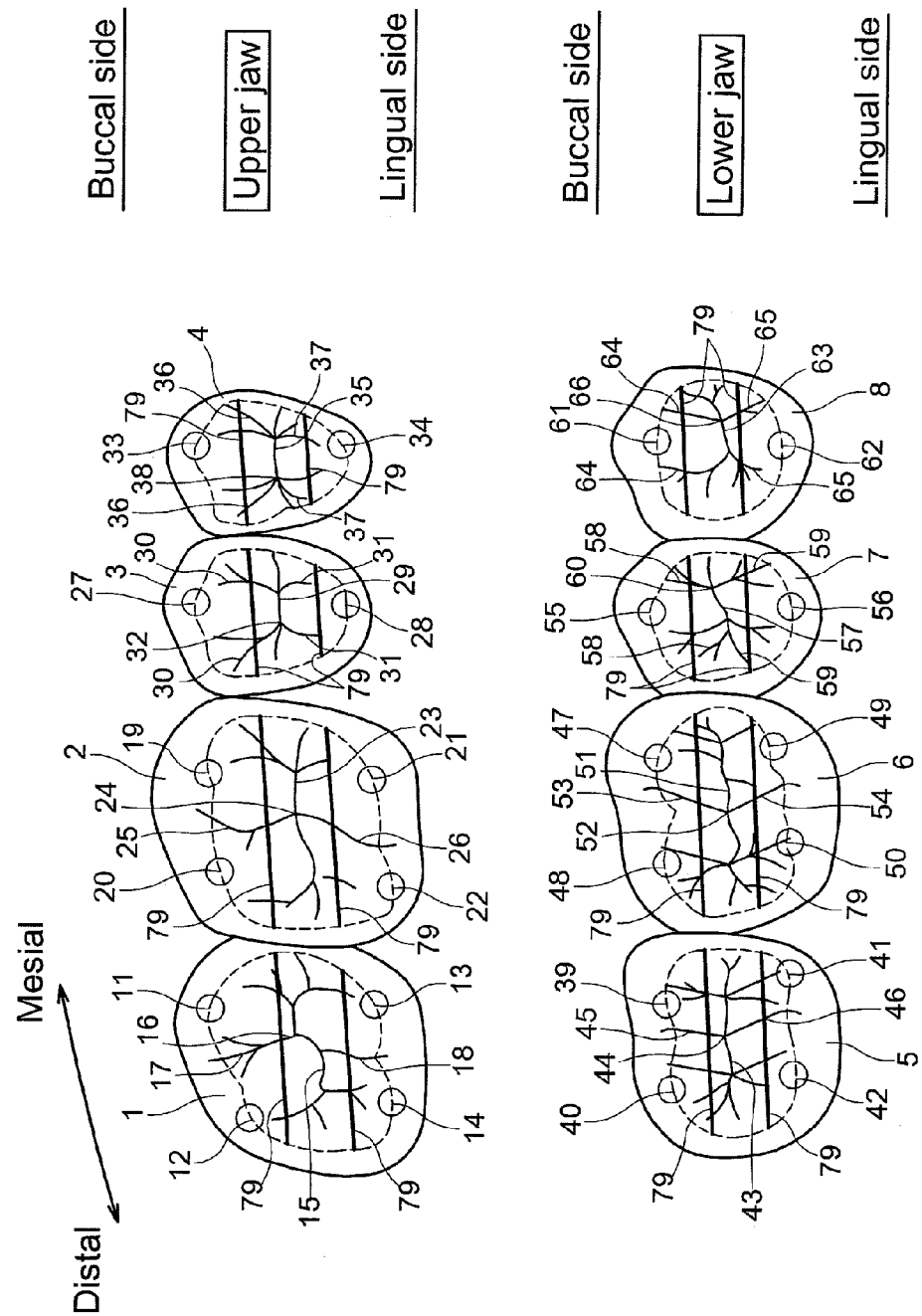
FIG. 5 is a plan view of upper molar teeth and lower molar teeth in a second embodiment.

FIG. 5 shows molar teeth 1 to 8 in a second embodiment. This second embodiment differs considerably from the first embodiment in that as the arrangement direction indication parts, there are provided indication lines 79 extending linearly in the mesiodistal direction in an occlusal plane view by coloring the occlusal planes. More specifically, the indication lines 79 are provided in each pair, positioned linearly in a correctly arranged state in the mutually adjacent molar teeth 1 to 4, and 5 to 8. Being extended linearly means, herein, either one straight line, or a line containing plural points extended intermittently (broken line, etc). Herein, the indication lines 79 are provided only within the occlusal planes, but may be provided to extend to the lateral side cross the occlusal planes.

The forming method of these indication lines 79 includes a method of coloring the forming position of the occlusal plane, and a method of coloring the region excluding the forming position so as to be expressed by the non-colored region. The colored region and the non-colored region are preferred to be different in color, but a same or similar color may be possible. However, in the case of same color or transparent color, it is preferred to use a color emitting light at a specified frequency, or developing color or emitting light in darkness. When using different colors, different colors such as black, red or blue may be used in each one of the artificial teeth 1 to 8, or in each one of the indication lines 79.

The coloring material for forming the indication lines 79 may be an oil-based ink and other material not deleted (peeled) in arrangement or transportation process. This coloring material may be naturally erased when worn in the oral cavity, or may be removed by using a chemical after the arrangement. The pigment of the coloring material may contain an organic material and a coloring material, and may preferably a material for oral use as designated as a food additive.

The artificial teeth 1 to 8 of the second embodiment thus configured are arranged, for example, as in the first embodiment, sequentially from the upper central incisor 73 to the maxillary second molar tooth 1 in the distal direction, and arranged sequentially from the lower central incisor 76 to the mandibular second molar tooth 5. At this time, the molar teeth 1 to 8 are adjusted so that the indication lines 79 of the molar teeth 1 to 3, 5 to 7 to be arranged later may be positioned linearly to the indication lines 79 of the previously arranged molar teeth 2 to 4, 6 to 8. Thereafter, the antagonist molar teeth 1 to 4, 5 to 8 are mutually adjusted so that the contour parts of the upper molar teeth 1 to 4 may be fitted into the grooves of the lower molar teeth 5 to 8. When arrangement and adjustment of all teeth are completed, the indication lines 79 are removed.

As described above, since the artificial teeth 1 to 8 of the second embodiment are provided with the colored indication lines 79 extended in the mesiodistal direction as arrangement direction indication parts, only by adjusting the indication lines 79 to be positioned linearly to the upper molar teeth 1 to 4 and the lower molar teeth 5 to 8, the teeth can be arranged in an accurate direction without requiring advanced skills and experiences. Moreover, it is recently required to keep the record of the course of treatment, and according to the second embodiment, it is possible to keep the record of the arrangement state by photographs or the like.

Figure 6:
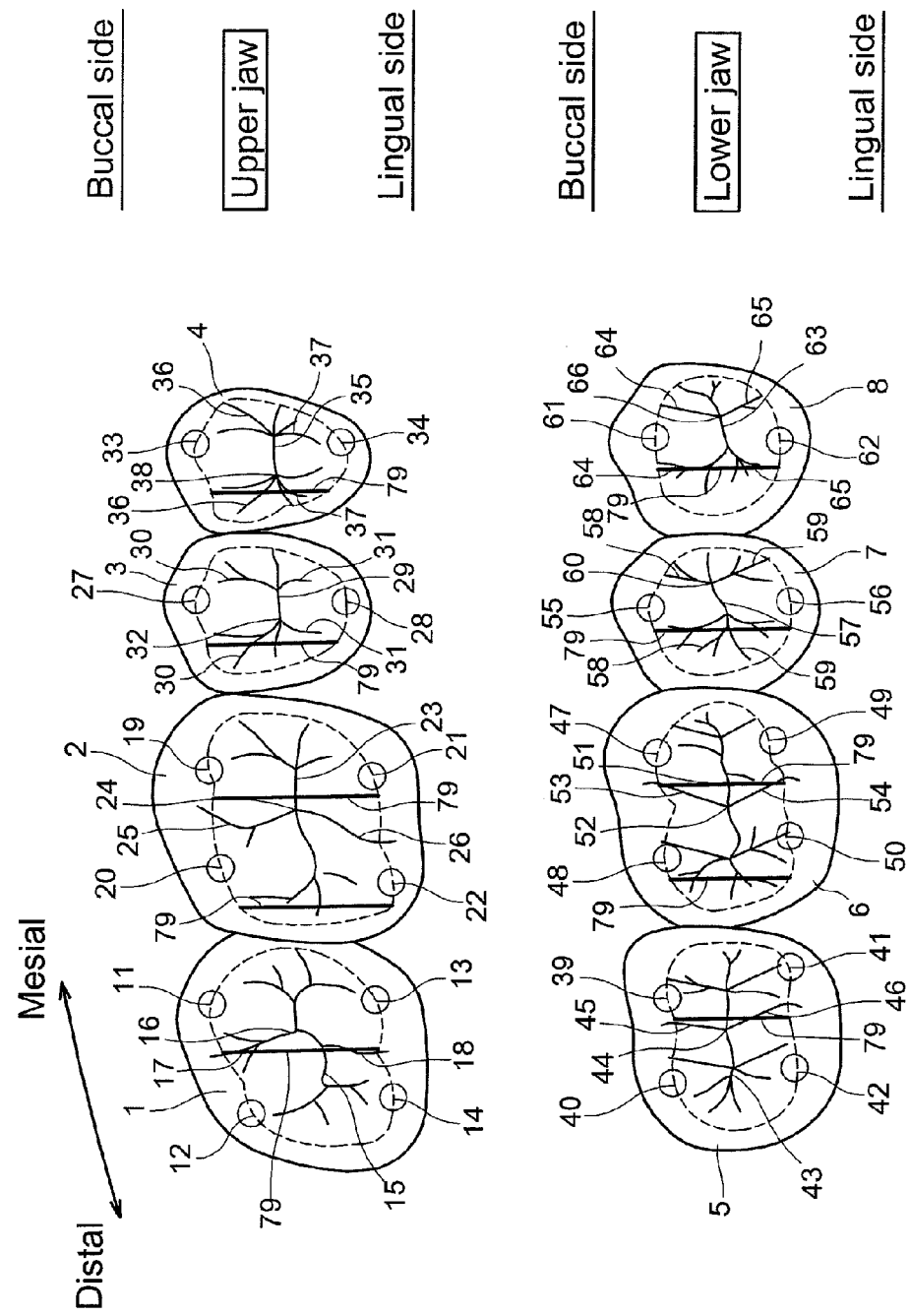
FIG. 6 is a plan view of upper molar teeth and lower molar teeth in a third embodiment.

FIGS. 6 to 8 show the artificial teeth 1 to 8 in a third embodiment. This third embodiment is significantly different from the second embodiment in that the indication lines 79 as the arrangement indication parts are formed by coloring the occlusal plane and are extended in the buccal-lingual direction. This embodiment, moreover, is different from the foregoing embodiments in that arrangement confirmation sheets 80A, 80B are additionally provided for checking the arrangement state in the arranged state of the artificial teeth 1 to 8. The indication lines 79 of the molar teeth 1 to 8 are provided away from the forming positions of the cusps. Since the first molar teeth 2, 6 are wide in the width in the mesiodistal direction, they are provided in a pair so as to be positioned near the mesial cusps 19, 21 and 47, 49 and the distal cusps 20, 22 and 48, 50.

The artificial teeth 1 to 8 of the third embodiment are arranged as in the first embodiment. The molar teeth 1 to 3, 5 to 7 to be arranged later are adjusted so that their indication lines 79 may be position in parallel to the indication lines 79 of the previously arranged molar teeth 2 to 4, 6 to 8. As a result, as in the foregoing embodiments, without requiring advanced skills and experiences, the teeth may be adjusted and arranged in specified positions.

In the embodiment, when arrangement of the artificial teeth 1 to 8 in the plates 9, 10 is completed, as shown in FIG. 7B and FIG. 8B, the arrangement state is confirmed by the arrangement confirmation sheets 80A, 80B. The arrangement confirmation sheets 80A, 80B are made of a base sheet 81, and confirm lines 82 to be overlapped with indication lines 79 in the normally arranged state. In this embodiment, two types are provided, for the upper molar teeth 1 to 4, and the lower molar teeth 5 to 8. The base sheet 81 is transparent or translucent so that the back side may be visible. The base sheet 81 is rectangular in shape formed of an elastically deformable resin. The confirm line 82 is formed in a line width similar to the indication line 79, and is opaque so that the back side may not be visible. The confirm line 82 is formed of an oil-based ink similar to the indication line 79, or formed of an opaque resin by double mold.

As shown in FIG. 7B and FIG. 8B, the arrangement confirmation sheet 80A is disposed at the occlusal plane side of the arranged upper molar teeth 1 to 4, and the arrangement confirmation sheet 80B is disposed at the occlusal plane side of the arranged lower molar teeth 5 to 8, and depending on whether the all indication lines 79 are overlapped with the confirm lines 82 or not, it can be determined whether the artificial teeth 1 to 4, 5 to 8 are arranged in normal state or not. If any deviation is found in the artificial teeth 1 to 8, they can be adjusted to the specified position. Accordingly, advanced skills and experiences are not required for the technician for arranging teeth. Of course, these arrangement confirmation sheets 80A, 80B can be used not only after arrangement of all upper molar teeth 1 to 4 and lower molar teeth 5 to 8, but also during arrangement thereof.

The artificial teeth of the invention are not limited to the configuration described in the embodiments alone, but may be changed in various forms.

For example, in the first embodiment, the contour lines 67a and indication grooves 67b of the upper molar teeth 1 to 4, and the buccal grooves 45, 53, 58, 64 and the lingual grooves 46, 54, 59, 65 of the lower molar teeth 5 to 8 are configured as arrangement direction indication parts showing the arrangement direction in the plates, but the buccal grooves 17, 25, 30, 36 and the lingual grooves 18, 26, 31, 37 of the upper molar teeth 1 to 4, and the contour lines of the lower molar teeth 5 to 8 may be configured as arrangement direction indication parts. In this way, the same action and effect as in the first embodiment may be obtained.

Incidentally, in the first embodiment, in particular, it may be difficult to identify the contour lines, the contour lines and the grooves may be colored as shown in the second and third embodiments. Of course, in the first embodiment, the both grooves of the upper molar teeth 1 to 4 and the lower molar teeth 5 to 8 may be configured as arrangement direction indication parts, and the contour lines of the both contour parts may be configured as arrangement direction indication parts.

Further, as in the third embodiment, even if the configuration of forming the arrangement confirmation sheets 80A, 80B may be the configuration of the first and second embodiments, or the combination of the first embodiment and second embodiment, or the combination of the second embodiment and third embodiment, it may be similarly applicable.

In the second embodiment, the indication lines 79, 79 of the adjacent teeth are positioned linearly, but when arrangement confirmation sheets are used, in particular, only by disposing in parallel or in line, it is not required to form to be positioned linearly. What is more, the artificial teeth 1 to 8 are provided in plural types slightly different in appearance depending on the shape of the remaining teeth of patient and the jaw shape, but when the arrangement confirmation sheets are used, all plural types may be formed to be identical in the position of the indication lines 79, and the arrangement confirmation sheets may be formed in one type only.

Although the present invention has been fully described by way of the examples with reference to the accompanying drawings, it is to be noted here that various changes and modifications will be apparent to those skilled in the art. Therefore, unless such changes and modifications otherwise depart from the spirit and scope of the present invention, they should be construed as being included therein.

What is claimed is:

1. A method of arranging a plurality of artificial molar teeth in a plate to be attached in an oral cavity as a dental prosthetic appliance, the method comprising:

positioning the artificial molar teeth in the plate, each artificial molar tooth of the artificial molar teeth comprising an arrangement direction indicator formed by a straight line crossing on an occlusal surface of the artificial molar tooth, the arrangement direction indicator showing an arrangement direction in the plate, said arrangement direction indicator passing through contour portions and grooves of the occlusal surface and extending linearly in an occlusal plane view, and said arrangement direction indicator comprising a line formed by coloring, wherein said line extends in a direction generally perpendicular or generally parallel to a mesiodistal direction when said artificial molar tooth is arranged in the plate;

placing an arrangement confirmation sheet over the occlusal surfaces of the artificial molar teeth positioned in the plate, the arrangement confirmation sheet comprising an elongated transparent and elastic sheet formed with line markings thereon; and adjusting the position of each artificial molar tooth of the artificial teeth on the plate so as to match said arrangement direction indicator on each artificial tooth with said line markings on the arrangement confirmation sheet.

2. The arranging method according to claim 1, wherein the arrangement direction indicator comprises two lines parallel to each other.

3. The arranging method according to claim 2, wherein, the lines of the arrangement direction indicators extend perpendicular to the mesiodistal direction when the artificial teeth are arranged in the plate.

4. The arranging method according to claim 2, wherein, the lines of the arrangement direction indicators extend parallel to the mesiodistal direction when the artificial teeth are arranged in the plate, the lines on the two adjacent teeth form a straight line.

* * * * *